(12) United States Patent
Yang et al.

(10) Patent No.: US 6,758,866 B2
(45) Date of Patent: Jul. 6, 2004

(54) ENHANCED COLOR DEPOSITION FOR HAIR WITH SEQUESTERING AGENTS

(75) Inventors: Jiang Yang, Ridgefield Park, NJ (US); John Brian Bartolone, Bridgeport, CT (US); Gabriela Wis-Surel, Cos Cob, CT (US); Alexander C Chan, Cranbury, NJ (US)

(73) Assignee: Unilever Home & Personal Care USA, Division of Conopco, Inc., Chicago, IL (US)

( * ) Notice: Subject to any disclaimer, the term of this patent is extended or adjusted under 35 U.S.C. 154(b) by 219 days.

(21) Appl. No.: 10/029,717

(22) Filed: Dec. 21, 2001

(65) Prior Publication Data

US 2003/0135935 A1 Jul. 24, 2003

(51) Int. Cl.$^7$ ................................................ A61K 7/13
(52) U.S. Cl. ...................... 8/405; 8/406; 8/410; 8/412; 8/421; 8/509; 8/515; 8/558; 8/584
(58) Field of Search ............................. 8/405, 406, 410, 8/412, 421, 509, 515, 558, 584

(56) References Cited

U.S. PATENT DOCUMENTS

| | | | |
|---|---|---|---|
| 5,876,464 A | 3/1999 | Lim et al. ........................ | 8/409 |
| 5,958,084 A * | 9/1999 | Shibata et al. .................. | 8/408 |
| 6,004,355 A * | 12/1999 | Dias et al. ...................... | 8/406 |
| 6,010,541 A | 1/2000 | de la Mettrie et al. ......... | 8/412 |
| 6,045,590 A * | 4/2000 | Lim et al. ....................... | 8/408 |
| 6,203,578 B1 | 3/2001 | Leduc et al. .................... | 8/405 |
| 6,309,426 B1 | 10/2001 | Dias et al. ...................... | 8/407 |
| 2002/0020029 A1 | 2/2002 | Kravtchenko et al. ......... | 8/405 |
| 2002/0147268 A1 * | 10/2002 | Rollat et al. ................. | 524/488 |

FOREIGN PATENT DOCUMENTS

| | | |
|---|---|---|
| DE | 21 19 231 A | 10/1972 |
| EP | 1048290 | 11/2000 |
| EP | 1106167 A2 | 6/2001 |
| EP | 1 147 763 A1 | 10/2001 |
| GB | 1334636 | 10/1973 |
| WO | 02/07473 A1 | 9/2002 |
| WO | 02/078661 A2 | 10/2002 |

OTHER PUBLICATIONS

International Search Report Application No. PCT/EP 02/13856 mailed Mar. 28, 2003.

* cited by examiner

Primary Examiner—Yogendra N. Cupta
Assistant Examiner—Eisa Elhilo
(74) Attorney, Agent, or Firm—Milton L. Honig

(57) ABSTRACT

Hair coloring compositions which comprise:
- (A) non-nitrogenous chelating agents from the group consisting of polyphosphate; phosphonates; hydroxy-carboxylates; polyacrylates; zeolite; and mixtures thereof;
- (B) an oxidative dye primary intermediate; and
- (C) an oxidative dye coupler;
- (D) and water
  are described.

The present invention also relates to a method for coloring hair which comprises contacting said hair with a hair coloring composition as described above.

12 Claims, No Drawings

ENHANCED COLOR DEPOSITION FOR HAIR WITH SEQUESTERING AGENTS

BACKGROUND OF INVENTION

It is desirable for hair coloring compositions to afford good color deposition. A problem with such compositions is that they must achieve deposition of a large amount of colorant and achieve an even color from root to tip of the hair fiber. It is an object of the present invention to provide a novel means for improving hair color deposition from hair coloring compositions.

A publication which is related to the field of this invention is as follows: EP 1 048290-A2 discloses oxidative, hair coloring compositions which color and condition hair, requiring lesser amounts of dye concentrations due to the presence of certain amphoteric, quaternized, conditioning polymers. The polymers contain repeating units from acrylic acid and methacrylamidopropyl trimethyl ammonium chloride, dimethyl diallyl ammonium chloride, or a mixture thereof.

U.S. Pat. No. 6,203,578 discloses the use of linear or cyclic silicon compounds containing at least one chromophoric group of quinone or azo type as direct dyes in dye compositions intended for dyeing human keratin fibres and in particular the hair. The invention also relates to novel silicon compounds and dye compositions containing them, as well as to the direct dyeing process. The compositions disclosed herein can contain sequestering agents.

U.S. Pat. No. 6,010,541 discloses an oxidation dye composition for keratin fibers, and in particular for human keratin fibers such as the hair, comprising, in a medium which is suitable for dyeing, at least one oxidation dye precursor and optionally one or more couplers, characterized in that it also comprises a nonionic amphiphilic polymer containing at least one fatty chain and at least one hydrophilic unit, and the invention also relates to the processes and dyeing devices using the said oxidation dye composition. The compositions disclosed herein can contain sequestering agents.

SUMMARY OF THE INVENTION

The present invention relates to permanent hair coloring compositions which comprise non-nitrogenous chelating agents such as polyphosphates or hydroxycarboxylates. Surprisingly, it has been found that hair coloring compositions which contain these chelators afford better color deposition on hair and cause color to be deposited more evenly on bleached, damaged, virgin hair than if the conventional EDTA is used.

The compositions of the present invention comprise:
(A) non-nitrogenous chelating agents selected from the group consisting of polyphosphate; phosphonates; hydroxycarboxylates; polyacrylates and its copolymer; zeolite; and mixtures thereof;
(B) an oxidative dye primary intermediate; and
(C) an oxidative dye coupler; and
(D) water.

The present invention also relates to a method for coloring hair which comprises contacting said hair with a composition of the invention.

DETAILED DESCRIPTION OF THE INVENTION

As used herein, % means weight %, unless otherwise indicated. As used herein the term chelator or chelating agent means a molecule that can form coordinate bonds to a single metal atom-that is, it is a sequestering agent. As used herein the term non-nitrogenous chelator or chelating agent means a molecule that is a chelating agent and that has no nitrogen. Preferred chelators or chelating agents mean a molecule that lacks an aminocarboxylic or an aminophosphonic acid group moiety. The compositions of the invention can be made by known methods or by methods that are analogous to known methods. The compositions of the present invention can be made from known starting materials or from starting materials that are analogous to known starting materials.

The compositions of the present invention comprise:
(A) a non-nitrogenous chelating agent selected from the group consisting of polyphosphates, phosphonates, hydroxycarboxylates, polyacrylates, zeolites and mixtures thereof;
(B) at least one oxidative dye primary intermediate; and
(C) at last one oxidative dye coupler; and
(D) water.

The invention also relates to a hair coloring mixture comprising:
(A) about 0.01 to about 3% of a non-nitrogenous chelating agent selected from the group consisting of polyphosphates, phosphonates, hydroxycarboxylates, polyacrylates, zeolites and mixtures thereof;
(B) about 0.01 to about 5% oxidative dye primary intermediate; and
(C) about 0.01 to about 5% oxidative dye coupler; and
(D) water.

The invention also relates to a hair coloring mixture comprising a mixture of:
(A) about 0.01 to about 3% of a non-nitrogenous chelating agent selected from the group consisting of polyphosphates, phosphonates, hydroxycarboxylates, polyacrylates, zeolites and mixtures thereof;
(B) about 0.01 to about 5% oxidative dye primary intermediate; and
(C) about 0.01 to about 5% oxidative dye coupler; and
(D) water.

The invention also relates to compositions as described above, which contain a non-amino chelating agent.

Sequestering agents have been used in hair colorant and developer as stabilizing agents. Because trace amount of metal may destabilize the colorant in a hair coloring composition, aminocarboxylic acids such as ethylenediamine tetraacetic acid (EDTA) have been traditionally used as sequestering agents in hair coloring compositions. It has been unexpectedly found that non-amino containing chelates such as polyphosphates and hydroxycarboxylates give better color deposition than that of amine containing chelates such as EDTA.

What follows now is a description of each of the ingredients which may be employed in the hair coloring compositions of the invention.

Non-Nitrogenous Chelating Agents and Non-Amino Chelating Agents

It has been unexpectedly discovered that certain chelating agents make hair colorant and hair dyeing compositions more efficient. These chelating agents make color deposition heavier and darker with the same amount of dye as compared to other chelating agents. Hence, these chelating agents allow the same target shade to be matched through the use of a lesser amount of dye. This allows for reduction in the cost of a hair coloring formula and/or reduces the exposure of consumers to these dyes, which may, for example, be allergens. As noted above, the present invention is related to a hair coloring composition comprising: a non-nitrogenous chelating agent selected from the group consisting of polyphosphates, phosphonates, hydroxycarboxylates, polyacrylates, zeolites and mixtures thereof.

Particular chelating agents that may be useful in the present invention for the purpose of enhancing dye color include polyphosphates such as pentasodium tripolyphosphate (STPP), potassium diphosphate, potassium pyrophosphate etc; non-amino containing phosphonic acid or its salts such as 1-hydroxyethane-1,1-diphosphonic acid (Dequest 2010, Astaris LLC); hydroxycarboxylates such as citric acid, gluconic acid, tartaric acid, 1,2,3,4-cyclopentanetetracarboxylic acid, O-carboxymethyl tartronic acid, O-carboxymethyloxysuccinic acid, oxidized carbohydrates and its salts etc; polyacrylates and their copolymers such as polyacrylic acid, acrylic acid/maleic acid copolymer, acrylic acid and sulfonated copolymer, polyaspartic polymer, poly (methylvinyl ether/maleic acid). Another class of useful chelating agents include ion exchangers such as Zeolites which are crystalline oxides of aluminum and silicon.

A non-amino chelator as described above, may optionally be mixed with a small amount of amino containing chelates without significantly reducing the color intensity achieved by the hair coloring compositions of the invention. Amino containing chelates can be aminocarboxylates such as nitrilotriacetate (NTA), ethylene diamine tetraacetate (EDTA), diethylene triamine pentaacetate (DTPA), and hydroxyethyl ethylene diamine triacetate (HEDTA), aminophosphonates such as amino trimethylene phosphate, ethylene diamine tetramethylene phosphonate.

Hair Colorants
Oxidative Hair Coloring Agents (Oxidative Dye Primary Intermediates)

Permanent hair dye compositions as described herein are compositions, which once applied to the hair are substantially resistant to wash-out. Wash-out as described herein is the process by which hair color is removed from the hair over time during a normal hair cleansing regimen.

Oxidative hair coloring agents which can be used in compositions of the invention can be selected from the group consisting of an aromatic diamine, an aminophenol, a polyhydric phenol, heterocyclic polyamines, a catchol and mixtures thereof. Oxidative hair coloring agents which can also be called oxidative dyes are described in more detail below.

Primary intermediates are chemical compounds, which by themselves will form a dye upon oxidation. A second class of intermediates is known as the secondary intermediates, also known as color modifiers or couplers and are used with other primary intermediates for specific color effects or to stabilize the color. Color couplers are described in more detail below.

The oxidation dye intermediates which are suitable for use in the compositions and processes herein include aromatic diamines, heterocyclic polyamines polyhydric phenols, aminophenols and derivatives of these aromatic compounds (e.g., N-substituted derivatives of the amines, and ethers of the phenols). Primary oxidation dye intermediates are generally colorless molecules prior to oxidation. The oxidation dye color is generated when the primary intermediate is activated and subsequently joined with a secondary intermediate (coupling agent), which is also generally colorless, to form a colored, conjugated molecule.

In general terms, oxidation hair dye precursors or intermediates include those monomeric materials which, on oxidation, form dimers or oligomers or polymers having extended conjugated systems of electrons in their molecular structure. Because of the new electronic structure, the resultant dimers or oligomers and polymers exhibit a shift in their electronic spectra to the visible range and appear colored. For example, oxidation dye precursors capable of forming colored molecules include materials such as anilines, which, on oxidation and further reaction with couplers, forms a series of dimers, trimers, and the like, ranging in color from green to black. Compounds such as p-phenylenediamine, which has two functional groups, are capable of oxidative coupling to yield higher molecular weight colored materials having extended conjugated electron systems. Color modifiers (couplers), such as those detailed hereinafter, are preferably used in conjunction with the primary intermediates herein. A representative list of primary intermediates suitable for use is found in Sagarin, "Cosmetic Science and Technology Interscience, Special Edn. Vol 2 pages 308 to 310, which is hereby incorporated by reference.

The hair coloring compositions of the invention may use one or more oxidative primary dye intermediates. Nonlimiting examples include:

p-phenylenediamine and its derivatives such as 2-methyl-p-phenylenediamine, p-phenylenediamine, N-phenyl-p-phenylenediamine, N,N-[bis-(2-hydroxyethyl)]-p-phenylenediamine, 2-chloro-p-phenylenediamine etc.

p-aminophenol and its derivatives such as: p-aminophenol, p-methylaminophenol, 2-methyl-4-aminophenol, 3-methyl-4-aminophenol, o-aminophenol and its derivatives such as o-aminophenol, 2,4-diaminophenol, 5-methyl-2-aminophenol etc.

heterocyclic derivatives such as 2,4,5,6-tetraaminopyrimidine, 4,5-diamino-1-methylpyrazole etc.

The primary intermediates can be used as a free base or in the form of an acid additive salt such as a hydrochloride, a hydrobromide, a sulfate or the like.

The typical aromatic diamines, polyhydric phenols, aminophenols, and derivatives thereof, described above as primary intermediates can also have additional substituents on the aromatic ring, e.g. halogen, and substituted and unsubstituted hydrocarbon groups, as well as additional substituents on the amino nitrogen, which is further substituted with (un)substituted alkyl and aryl groups.

Nonlimiting examples of suitable aromatic diamines, aminophenols, polyhydric phenols and derivatives thereof, respectively, are the following compounds:

o-phenylenediamine,
1,3,5-triaminobenzene,
2-hydroxy-p-phenylenediamine,
N, N-diisopropyl-p-phenylenediamine bicarbonate,
N,N-dimethyl-p-phenylenediamine,
N-ethyl-N'-(2-propenyl)-p-phenylenediamine,
N-phenyl-p-phenylenediamine,
N-phenyl-N-benzyl-p-phenylenediamine,
N-ethyl-N'-(3-ethylphenyl)-p-phenylenediamine,
2,5-toluenediamine,
2-ethyl-p-phenylenediamine,
2-(2-bromoethyl)-p-phenylenediamine,
2-phenyl-p-phenylenediamine,
4-(2,5-diaminophenyl)benzaldehyde,
2-benzyl-p-phenylenediamine,
2-(4-nitrobenzyl)-p-phenylenediamine, 2-(4-methylphenyl)-p-phenylenediamine,
2-(2,5-diaminophenyl)-5-methylbenzoic acid,
2-methoxy-p-phenylenediamine,
2,3-dimethyl-p-phenylenediamine,
2,5-dimethyl-p-phenylenediamine,
2-methyl-5-methoxy-p-phenylenediamine,
2,6-methyl-5-methoxy-p-phenylenediamine,
3-methyl-4-amino-N, N-diethylaniline,
N,N-bis-(2-hydroxyethyl)-p-phenylenediamine,
3-methyl-4-amino-N,N-bis-(2-hydroxyethyl)aniline,
3-chloro-4-amino-N,N-bis-(2-hydroxyethyl)aniline,
4-amino-N-ethyl-(N-piperidonoethyl)aniline,
3-methyl-4-amino-N-ethyl-N-β-(piperidinoethyl)aniline,
4-amino-N-ethyl-N-(morpholinoethyl)aniline,
4-amino-N-ethyl-N-(acetylaminoethyl)aniline,
4-amino-N-(methoxyethyl)aniline,
3-methyl-amino-N-ethyl-N-(2-acetylaminoethyl)aniline,
4-amino-N-ethyl-N-(mesylaminoethyl)aniline,
3-methyl-4-amino-N-ethyl-N-(β-mesylaminoethyl) aniline,
4-amino-N-ethyl-N-(-sulfoethyl)aniline,
3-methyl-4-amino-N-ethyl-N-(β-sulfoethyl)aniline,
N-(4-aminophenyl)morpholine,
N-(4-aminophenyl)piperidine,
2-isopropyl-p-phenylenediamine,
N,N-bis-(2-hydroxyethyl)-p-phenylenediamine sulfate,
o-aminophenol,
p-aminophenol,
2-iodo-p-aminophenol,
3,4-dihydroxyaniline,
3,4-diaminophenol,
N,N-diisopropyl-p-aminophenol,
N-methyl-N-(1-propenyl)-aminophenol,
N-phenyl-N-benzyl-p-aminophenol sulfate,
N-methyl-N-(3-ethylphenyl)-p-aminophenol,
(2-hydroxy-5-aminophenyl)acetaldehyde,
2-methyl-p-aminophenol,
(2-hydroxy-5-aminophenyl)acetic acid,
3-(2-hydroxy-5-aminophenyl-1-propene,
3-(2-hydroxy-5-aminophenyl)-2-chloro-1-propene,
2-phenyl-p-aminophenol palmitate,
2-benzyl-p-aminophenol,
2-(4-chlorobenzyl)-p-aminophenol perchlorate,
2-(4-methylphenyl)-p-aminophenol,
2-(2-amino-4-methylphenyl)-p-aminophenol,
p-methoxyaniline,
di-(2-aminoethyl-4-aminophenyl) ether,
di-(2-hydroxyethyl-4-aminophenyl) ether,
(4-aminophenoxy)acetaldehyde,
(4-aminophenoxy)acetic acid,
(4-aminophenoxy)methanesulfonic acid,
1-propenyl-4-aminophenyl ether isobutyrate,
di-(2-amino-propenyl-4-aminophenyl) ether,
di-(2-hydroxy-propenyl-4-aminophenyl) ether,
N-methyl-p-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
3-(3,4-dihydroxyphenyl)-alanine (DOPA)
2,5-dimethyl-4-aminophenol,
2-hydroxymethyl-4-aminophenol,
3-hydroxymethyl-4 aminophenol,
o-hydroxyphenol (catechol),
p-hydroxyphenol (hydroquinone),
4-methoxyphenol,
2-methoxyphenol,
4-(2-chloroethoxy)phenol,
4-(2-propenoxy)phenol,
4-(3-chloro-2-propenoxy)phenol,
2-chloro-4-hydroxyphenol (2-chlorohydroquinone),
2-amino-4-hydroxyphenol,
1,2,3-trihydroxybenzene (pyrogallol),
3-ethyl-4-hydroxyphenol,
3-(2-nitroethyl)-4-hydroxyphenol,
3-(2-propenyl)-4-hydroxyphenol,
3-(3-chloro-2-propenyl)-4-hydroxyphenol,
2-phenyl-4-hydroxyphenol,
2-(4-chlorophenyl)-4-hydroxyphenol,
2-benzyl-4-hydroxyphenol,
2-(2-nitrophenyl)-4-hydroxyphenol,
2-(2-methylphenyl)-4-hydroxyphenol,
2-(2-methyl-4-chlorophenyl)-4-hydroxyphenol,
2-methoxy-4-(1-propenyl)phenol,
2,5-dimethoxyaniline,
2,5-diaminopyridine,
2-hydroxy-5-aminopyridine,
2-amino-3-hydroxypyridine,
tetraaminopyrimidine,
1,2,4-trihydroxybenzene
1,2,4-trihydroxy-5-($C_1$–$C_6$-alkyl)benzene,
4-aminoresorcinol,
2-amino-1,4-dihydroxybenzene,
2-amino-4-methoxyphenol,
2,4-diaminophenol,
3-methoxy-1,2-dihydroxybenzene,
4,6-dimethoxy-3-amino-1-hydroxybenzene,
2,6-dimethyl-4-(p-hydroxyphenyl)amino]phenol and salts thereof;
4-chloro-5,8-dimethoxy-6-methynaphth-1-ol,
4-chloro-5,8-dimethoxynaphth-1-ol,
4-acetoxy-5-chloro-6-methyl-7-acetyl-8-hydroxynaphth-1-ol,
4-acetoxy-8-benzyloxynaphth-1-ol,
4-benzyloxynaphth-1-ol,
4,8-dibenzyloxy-6-methylnaphth-1-ol,
4,8-dibenzyloxynaphth-1-ol,
4-benzyloxy-8-(2-chloro)ethoxynaphth-1-ol,
4-benzyloxy-8-isopropyloxynaphth-1-ol,
4-benzyloxy-8-methoxynaphth-1-ol,
4-(2-bromo)ethoxynaphth-1-ol,
4-(2-bromo)ethoxy-5-methoxynaphth-1-ol, 4-(2-bromo)ethoxy-8-methoxynaphth-1-ol,
4-(2-chloro)ethoxynaphth-1-ol,
4-(2-chloro)ethoxy-8-methoxynaphth-1-ol,
4-(2-methoxy)ethoxynaphth-1-ol,
(4-hydroxy-1-naphthyl)oxyacetic acid,
4-methoxynaphth-1-ol,
4-methoxy-5-chloronaphth-1-ol,
4-methoxy-5-chloro-8-benzyloxynaphth-1-ol,
4,8-dimethoxy-5-chloronaphth-1-ol,
4-methoxy-5-methylnaphth-1-ol,
4-methoxy-5-benzyloxynaphth-1-ol,
4-methoxy-5-benzyloxy-7-methylnaphth-1-ol,
4-methoxy-5-hydroxynaphth-1-ol,
4-methoxy-5-hydroxy-7-methylnaphth-1-ol,
4-methoxy-5-isopropyloxynaphth-1-ol,
4,5-dimethoxynaphth-1-ol,
4,5-dimethoxy-6-benzyloxynaphth-1-ol,
4,5-dimethoxy-7-methynaphth-1-ol,
4,5-dimethoxy-8-chloronaphth-1-ol,
4-methoxy-6-methynaphth-1-ol,
4-methoxy-6-methyl-7-acetyl-8-hydroxynaphth-1-ol,
5-4-dimethoxy-6,7-dimethylnaphth-1-ol,
4-methoxy-6-methyl-8-benzyloxynaphth-1-ol,
4-methoxy-6-methyl-8-hydroxynaphth-1-ol,
4,8-dimethoxy-6-methylnaphth-1-ol,
4-methoxy-6-ethoxynaphth-1-ol,
4-methoxy-6,7-diethoxynaphth-1-ol,
4-methoxy-7-methylnaphth-1-ol,
4,8-dimethoxy-7-benzyloxynaphth-1-ol,
4-methoxy-7-ethoxynaphth-1-ol,
4-methoxy-8-chloronaphth-1-ol,
4-methoxy-8-methynaphth-1-ol,
4-methoxy-8-benzyloxynaphth-1-ol,
4-methoxy-8-hydroxynaphth-1-ol,
4-methoxy-8-isopropyloxynaphth-1-ol,
4,8-dimethoxynaphth-1-ol,
4-ethoxynaphth-1-ol,
4-propyloxynaphth-1-ol,
4-isopropyloxynaphth-1-ol,
4-butoxynaphth-1-ol,
4-isobutoxynaphth-1-ol,
4-sec-butoxynaphth-1-ol,
4-isoamoxynaphth-1-ol,
4-(2-chloroisopropyloxy)naphth-1-ol,
4-cyclohexyloxynaphth-1-ol,
4-octyloxynaphth-1-ol,
4-(2-chloropropoxy)naphth-1-ol,
5-methoxynaphth-1-ol,
5,8-dimethoxy-6-methylnaphth-1-ol,
5,8-dimethoxy-6,7-dichloronaphth-1-ol,
5,8-dimethoxy-7-methy-inaphth-1-ol,
5,8-diacetoxynaphth-1-ol, and
7-methoxynaphth-1-ol.
    4-methoxynaphth-1-ol,
4-ethoxynaphth-1-ol,
4-isopropyloxynaphth-1-ol,
4,8-dimethoxynaphth-1-ol.
4,5-dihydroxyindoles (DHI)
4,5-dihydroxyindoline
4,5-dihydroxyindolecarboxylic acid (DHICA)

Oxidative Dye Couplers (Secondary Intermediates)

Suitable oxidative dye couplers may be included in compositions of the invention. Nonlimiting examples include:
    phenol derivatives and resorcinol, naphthol and their derivatives such as resorcinol, 1-naphthol, 2-methyl-1-naphthol, 4-chlororesorcinol etc.

The oxidation dye couplers can be used herein alone or in combination with other oxidation dye couplers mentioned above. The choice of a single dye coupler (precursor) will be determined by the color, shade and intensity of coloration which is desired. The following are preferred oxidation dye couplers which can be used herein, singly or in combination, to provide oxidation hair dyes having a variety of shades ranging from ash blonde to black; these are: pyrogallol, resorcinol, m-phenylenediamine, m-aminophenol, 4-amino-2-hydroxytoluene, 1,hydroxynapthalene, 2-methyl resorcinol, 2,6-diaminepyridine, 4-hydroxyindole, 6-hydroxyindole, 4-hydroxyindoline, 6-hydroxyindoline, 4,5-diaminepyrazole, and 1-phenyl-3-methyl-pyazolone. These can be used in the molecular form or in the form of peroxide-compatible salts, as detailed above.

Conditioners

Conditioners may be employed in compositions of the invention. Suitable conditioning agents are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the formula:

$$[N(R_1)(R_2)(R_3)(R_4)]^+(X)^-$$

in which $R_1$, $R_2$, $R_3$, and $R_4$ are independently selected from (a) H or an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and $X^-$ is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention can include monoalkyl quaternary ammonium compounds in which the alkyl chain length is C8 to C14.

Suitable examples of such materials correspond to the formula:

$$[N(R_5)(R_6)(R_7)(R_8)]^+(X)^-$$

in which $R_5$ is a hydrocarbon chain having 8 to 14 carbon atoms or a functionalized hydrocarbon chain with 8 to 14 carbon atoms and containing ether, ester, amido or amino moieties present as substituents or as linkages in the radical chain, and $R_6$, $R_7$ and $R_8$ are independently selected from (a) hydrocarbon carbonyl chains of from 1 to about 4 carbon atoms, or (b) functionalized hydrocarbon chains having from 1 to about 4 carbon atoms and containing one or more aromatic, ether, ester, amido or amino moieties present as substituents or as linkages in the radical chain, and $X^-$ is a salt-forming anion such as those selected from halogen, (e.g. chloride, bromide), acetate, citrate, lactate, glycolate, phosphate, nitrate, sulphate, and alkylsulphate radicals.

The functionalised hydrocarbon chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbon chains $R_1$ have 8 to 22 carbon atoms, most preferably 18 carbon atoms.

Examples of suitable cationic surfactants include:

quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldi-methylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., Quaternium -5

Quaternium -31

Quaternium -18 and mixtures thereof.

In the compositions of the invention, the level of cationic surfactant is preferably from 0.01 to 10, more preferably 0.05 to 10, most preferably 0.1 to 5 wt % of the total composition.

The compositions of the present invention may contain a humectant. The humectants may be selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 10%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR and SUPEROL available from The Procter & Gamble Company, CRODEROL GA700 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-64 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimara Pharcos; sodium adenosine phosphate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, R-HODOCAP series available from Rhone-Poulenc, and DEXPEARL available from Tomen; and polyethylene glycols with the tradename CARBOWAX series available from Union Carbide.

Solvents

Water is the preferred principal diluent for the compositions according to the present invention. As such, the compositions of present invention may also include one or more solvents as additional diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a particularly preferred group includes ethanol, benzyl alcohol, isopropanol, n-propanol, butanol, glycols, glycol ethers such as propylene glycol, propylene glycol monomethyl ether, dipropylene glycol, diethylene glycol ether, ethylene glycol monoethyl ether, and mixtures thereof in concentrations ranging from about 0.5% to 20% and more preferably about 2% to about 10% by total weight of the compositions.

The compositions of the invention may also include the following materials.

Buffering Agents

The coloring compositions of the present invention may have a pH in the range of from about 7.5 to about 11, more preferably from about 8 to about 11.

As herein before described the preferred coloring compositions of the present invention may contain one or more buffering agents and/or hair swelling agents (HSAs) to adjust the pH to the desired level. Several different pH modifiers can be used to adjust the pH of the final composition or any constituent part thereof.

These can include ammonia and its salt, carbonates, phosphates, hydroxides, amines, etc.

Thickeners

The composition containing one or more oxidative hair coloring agents of the present invention (coloring compositions) may additionally include a thickener at a level of from about 0.05 % to about 20%, preferably from about 0.1% to about 10%, more preferably from about 0.5% to about 5% by weight. Thickening agents suitable for use in the compositions of the invention may be selected from the group consisting of oleic acid, cetyl alcohol, oleyl alcohol, sodium chloride, cetearyl alcohol, stearyl alcohol, and synthetic thickeners, and mixtures thereof.

Guar gum, hydroxy alkylcellulose, polyacrylates, carbopols, etc. are also included.

Surfactant Materials

The compositions of the present invention may additionally contain a surfactant system. Surfactants which may be employed include anionic, cationic, nonionic, amphoteric or zwitterionic surfactants. Suitable surfactants for inclusion in the compositions of the invention can have a lipophilic chain length of from about 8 to about 22 carbon atoms and can be selected from the group consisting of anionic, cationic, nonionic, amphoteric, zwitterionic surfactants and mixtures thereof.

(i) Anionic Surfactants

Anionic surfactants suitable for inclusion in the compositions of the invention include alkyl sulphates, ethoxylated alkylsulphates, alkyl glyceryl ether sulfonates, methyl acyl taurates, fatty acyl glycinates, N-acyl glutamates, acylisethionates, alkyl sulfosuccinates, alkyl ethoxysulphosuccinates, alpha-sulfonated fatty acids, their salts and/or their esters, ethoxy alkyl carboxylates, alkyl phosphate esters, ethoxylated alkyl phosphate esters, alkyl sulphates, acylsarcosinates and fatty acid/protein condensates, and mixtures thereof. Alkyl and/or acyl chain lengths for these surfactants are C12–C22, preferably C12–C18.

(ii) Nonionic Surfactants

The compositions of the invention can also comprise a water-soluble nonionic surfactants.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives.

Preferred for use herein are polyethyleneglycol based polyethoxylated $C_9$–$C_{15}$ fatty alcohol nonionic surfactants containing an average of from about 5 to about 50 ethyleneoxy moieties per mole of surfactant.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include: alkyl betaines, alkyl sultaines, alkyl amphoacetates, alkyl amphodiacetates, alkyl amphopropionates, and alkyl amphodipropionates.

(iv) Zwitterionic Surfactants

Water-soluble auxiliary zwitterionic surfactants suitable for inclusion in the compositions of the present invention include alkyl betaines Water-soluble auxiliary sultaine surfactants suitable for inclusion in the compositions of the present invention include alkyl sultaines. Preferred for use herein is coco amido propylhydroxy sultaine.

Water-soluble auxiliary amine oxide surfactants suitable for inclusion in the compositions of the present invention include alkyl amine oxides and amido amine oxides. Preferred amine oxides include cocoamidopropylamine oxide, lauryl dimethyl amine oxide and myristyl dimethyl amine oxide.

(v) Cationic Surfactants

Examples of cationic surfactants include: quaternary ammonium hydroxides, e.g., alkyltrimethylammonium hydroxide wherein the alkyl group has about 8 to 22 carbon atoms, for example, octyltrimethylammonium hydroxide, dodecyltrimethylammonium hydroxide, hexadecyltrimethylammonium hydorxide, cetyltrimethylammonium hydroxide, octyldimethylbenzelammonium hydroxide, decyldimethylbenzylammonium hydroxide, stearyldimethylbenzylammonium hydroxide, didodecyldimethylbenzylammonium hydroxide, dioctadecyldimethylbenzylammonium hydroxide, tallow trimethylammonium hydroxide, coco trimethylammonium hydroxide, and the corresponding salts thereof, e.g., chloide, cetylpyridinium hydroxide, and the corresponding salts thereof, e.g., chloride, cetyl pyridinium hydroxide or salts thereof, e.g., chloride, Quaternium-5, Quaternium-18, Quaternium-31, Quaternium-37, and mixtures thereof.

Optional Ingredients

The compositions of the present invention may also contain perfumes, antioxidants, dispersing agents, opacifiers, and preservatives and other materials which are customarily found in hair colorant compositions.

A dual package which can be employed in products and kits which contain compositions of the present invention is described in U.S. Pat. No. 6,082,588 to Markey et al which is hereby incorporated by reference.

Kit Containing an Instruction Sheet

The present invention also relates to a kit for carrying out the hair coloring method of the invention. The kit comprises a developer solution, which is usually an aqueous 2–9% hydrogen peroxide solution a dye solution and a post treatment solution, each in a separate container or in a dual container, as described herein. The kit also contains written instructions that explain how the compositions of the invention are used.

The consumer admixes the components of the kit according to written instructions, to obtain the aqueous reaction mixture. The admixture may be conducted in a separate vessel external to the kit, or may take place in a container of the kit adapted to provide sufficient head space for mixing. The components that are mixed are the developer composition and the dye composition. The reactants may also be admixed on the hair of the user. Essentially upon mixing, reaction of the dye and the developer will commence. After treatment for a desired time the mixture of hair developer and hair dye is removed, preferably with water or a conventional shampoo or a conventional conditioning shampoo.

The following are nonlimiting examples of hair coloring compositions of the present invention which have been made.

EXAMPLE 1

The different hair colorants with EDTA or sodium triphosphate (STPP) are shown, and were made with the following formula: water 91.30%, dye precursors 1.55%, $NH_4OH$ (29% active)6%, sodium isoascorbate 0.15%. These ingredients were mixed together and stirred until dissolved.

Three different color shades were demonstrated with combinations of p-aminophenol (PAP), 4-amino-o-cresol (PAOC), p-phenylenediamine(PPD) and Resorcinol (RS) (made by Lowenstein, Brooklyn, N.Y.). The color developer used was 6% $H_2O_2$. The colorant and developer were mixed in a 1:2 ratio before applying on hair. The hair was dyed with the above mixture for 30 minutes, followed by washing with water and shampooing for 30 seconds, and then drying. The color was measured by Hunter's L.a.b value. Standard derivation is less than 1.0 for an average of 5 measurements. The results are given in table 1.

It can be seen that the color is significantly lighter (that is, not as much color was deposited) in the presence of EDTA as compared to the same formula with polyphosphate, sodium triphosphate STPP (used at the same mole per cent). The color difference is most obvious for red shade.

TABLE I

The colorant with different sequestering agent (6% NH4OH, 1% sodium sulfite, pH = 10) and their L.a.b color value on Hair.

| | | Color/Shade | | | | | | |
|---|---|---|---|---|---|---|---|---|
| | | Red Color (0.75% PAP, 0.8% PAOC) | | | Green Brown Color (0.375% PPD, 0.40% RS) | | Violet Color (0.375% PPD, 0.45% PAOC) | |
| Color Parameter | Undyed Hair | 0.60% EDTA | 0.58% STPP | 1.0% Polyacrylat (alcosphere 602N) | 0.60% EDTA | 0.58% STPP | 0.60% EDTA | 0.58% STPP |
| L | 78.3 | 52.1 | 36.4 | 38.4 | 45.1 | 40.0 | 36.4 | 25.4 |
| A | −2.0 | 26.5 | 31.0 | 34.5 | 3.6 | 4.0 | 22.8 | 22.7 |
| B | 8.4 | 31.0 | 30.3 | 36.2 | 16.1 | 13.7 | −3.2 | −2.0 |
| ΔE | 0 | 44.8 | 57.7 | 60.8 | 34.5 | 39.1 | 50.0 | 59.3 |
| % Improvement compared to EDTA | 0 | | 28.8% | 36% | | 13.3% | | 18.6% |

*ΔE total color difference from undyed hair: $\sqrt{(\Delta L^2 + \Delta a^2 + \Delta b^2)}$

EXAMPLE 2

Above trend continued when full formulations were tested with two dye pairs, PAP/PAOC (red), PPD/RS (green brown) and a complete dark red brown shade as shown in Table II below. (Rodol BLFX: p-Toluenediamine sulfate; Rodol GRAY HED: N,N-bis-hydroxyethyl-p-phenylenediamine sulfate; Rodol PMP: 1-phenyl-3-methyl-5-pyrazolone; Rodol MRP: 2-methylresorcinol; Rodol MPDS: m-phenylenediamine sulfate; Rodol 2G: o-aminophenol)

TABLE II

The colorant formulations with different sequestering agent (pH = 10) and their L.a.b color value on Hair.

| | # Shade | | | | | | | | |
|---|---|---|---|---|---|---|---|---|---|
| | 1. Red Color | | | 2. Green Brown color | | | 3. Dark Red Brown color | | |
| Ingredients (w %) | #1a no chelate | #1b with EDTA | #1c with STPP | #2a no chelate | #2b with EDTA | #2c with STPP | #3a no chelate | #3b with EDTA | #3c with STPP |
| EDTA | | 0.6 | | | 0.6 | | | 0.600 | |
| STPP | | | 0.58 | | | 0.58 | | | 0.580 |
| PAP | 0.75 | 0.75 | 0.75 | | | | 0.600 | 0.600 | 0.600 |
| PAOC | 0.80 | 0.80 | 0.80 | | | | 0.720 | 0.720 | 0.720 |
| PPD | | | | 0.75 | 0.75 | 0.75 | | | |
| RS | | | | 0.80 | 0.80 | 0.80 | | | |
| Rodol BLFX | | | | | | | 0.407 | 0.407 | 0.407 |
| Rodol PMP | | | | | | | 0.100 | 0.100 | 0.100 |
| Rodol GREY HED | | | | | | | 0.120 | 0.120 | 0.120 |
| Rodol 2G | | | | | | | 0.005 | 0.005 | 0.005 |
| Rodol MRP | | | | | | | 0.500 | 0.500 | 0.500 |
| Rodol MPDS | | | | | | | 0.001 | 0.001 | 0.001 |
| Oleic acid | 8.6 | 8.6 | 8.6 | 8.6 | 8.6 | 8.6 | 8.600 | 8.600 | 8.600 |
| PEG 3 Cocamine | 8.0 | 8.0 | 8.0 | 8.0 | 8.0 | 8.0 | 8.000 | 8.000 | 8.000 |
| Dihydroxyethyl soyamine dioleate | 22.2 | 22.2 | 22.2 | 22.2 | 22.2 | 22.2 | 22.200 | 22.200 | 22.20 |
| Isopropanol | 12.5 | 12.5 | 12.5 | 12.5 | 12.5 | 12.5 | 12.500 | 12.500 | 12.50 |
| Propylene glycol | 8.6 | 8.6 | 8.6 | 8.6 | 8.6 | 8.6 | 8.600 | 8.600 | 8.600 |
| Fragrance | 0.50 | 0.50 | 0.50 | 0.50 | 0.50 | 0.50 | 0.500 | 0.500 | 0.500 |
| Sodium sulfite | 1.0 | 1.0 | 1.0 | 1.0 | 1.0 | 1.0 | 1.000 | 1.000 | 1.000 |
| Sodium isoascorbate | 0.15 | 0.15 | 0.15 | 0.15 | 0.15 | 0.15 | 0.150 | 0.150 | 0.150 |
| NH4OH | 6.0 | 6.0 | 6.0 | 6.0 | 6.0 | 6.0 | 12.000 | 12.000 | 12.00 |
| Water | 30.9 | 30.3 | 30.32 | 30.9 | 30.3 | 30.32 | 24.500 | 23.900 | 23.92 |
| Total | 100. | 100. | 100.0 | 100. | 100. | 100. | 100.00 | 100.00 | 100.0 |
| Color Parameter | #1a | #1b | #1c | #2a | #2b | #2c | #3a | #3b | #3c |
| L | 46.5 | 53.3 | 46.3 | 26.4 | 27.8 | 25.0 | 36.2 | 44.6 | 36.7 |
| A | 30.1 | 24.6 | 29.4 | 4.1 | 4.3 | 4.4 | 14.5 | 15.8 | 14.2 |

TABLE II-continued

The colorant formulations with different sequestering agent (pH = 10) and their L.a.b color value on Hair.

| B  | 34.1 | 30.0 | 34.0 | 13.9 | 14.0 | 13.6 | 13.1 | 15.4 | 12.8 |
|----|------|------|------|------|------|------|------|------|------|
| ΔE | 52.0 | 42.5 | 51.6 | 52.4 | 51.1 | 53.9 | 45.4 | 38.7 | 44.8 |

*ΔE is difference of color with undyed hair (L: 78.25, a: −2.04, b: 8.41)

EXAMPLE 3

Other chelates are shown in Table III. It can be seen that amino containing chelates such as EDTA, diethylenetriamine pentaacetic acid (DTPA), Dequest 2006 (aminotrimethylene-phosphonic acid, made by Astris LLC, St. Louis, Mo.) or combinations including amino containing chelates gave lighter color. Dequest 2016® (Hydroxyethylidenediphosphonic acid, made by Astris LLC, St. Louis, Mo.) and citric acid gave more color.

the difference in water hardness in different regions. This can be clearly seen by presoaking hair in samples of water of differing hardness for a half-hour, and then dyeing with a dye solution as shown in Table IV for two different shades. The colors of the tresses treated by compositions without chelating agents have considerable differences in color intensity. Without chelating agents, the color intensity of tresses treated in harder water is higher than the color intensity of tresses treated in softer water. On the other hand, the sequestering agents EDTA or polyphosphate eliminate

TABLE III

Colorants with different sequestering agents (0.75% PAP, 0.8% PAOC, 6% NH4OH, 1% sodium sulfite, pH = 10) and their L.a.b color values on Hair.

| | | | # Shade/ | | | | |
|---|---|---|---|---|---|---|---|
| Color Parameter | Undyed Hair | 0.40% EDTA | 0.4% EDTA & 0.55% Dequest 2016D | 1.0% Dequest 2006 | 0.2% DTPA | 0.55% Dequest 2016D | 0.50% Citric acid |
| L | 78.3 | 53.1 | 51.7 | 50.9 | 52.6 | 38.8 | 38.3 |
| a | −2.0 | 28.3 | 28.0 | 30.8 | 29.3 | 35.6 | 34.3 |
| b | 8.4 | 31.8 | 32.3 | 34.7 | 32.8 | 36.6 | 33.7 |
| ΔE | 0 | 45.8 | 46.7 | 50.2 | 47.3 | 61.4 | 59.6 |
| % Improvement Compared to EDTA | | | 2.0% | 9.6% | 3.3% | 34.1% | 30.1% |

EXAMPLE 4

Besides complexing with metal impurities, sequestering agents can also minimize color differences which arise from this difference. Hence, it is essential to have a sequestering agent in the product to achieve the same color tone regardless of the source of water used.

TABLE IV

Prewashing of hair with water of different hardness and then dyed with colorant containing different chelating agents, 0.75% PAP, 0.8% PAOC, 5% oleic acid, 12% isopropanol, 6% NH4OH, 1% sodium sulfite on Nature White Hair at pH = 10.

| | | Water | | | | | |
|---|---|---|---|---|---|---|---|
| | | No Chelates | | 0.6% EDTA | | 0.58% STPP | |
| Color Parameter | Undyed Hair | Water A: 50 ppm as of CaCO3 | Water B: 250 ppm as of CaCO3 | Water A: 50 ppm as of CaCO3 | Water B: 250 ppm as of CaCO3 | Water A: 50 ppm as of CaCO3 | Water B: 250 ppm as of CaCO3 |
| L | 71.2 | 46.9 | 42.0 | 53.5 | 53.8 | 43.9 | 44.5 |
| A | 2.0 | 26.0 | 27.3 | 21.9 | 22.5 | 28.0 | 27.1 |
| B | 24.6 | 31.9 | 30.9 | 30.8 | 30.5 | 32.5 | 31.3 |
| ΔE | 0 | 34.9 | 39.1 | 27.3 | 27.5 | 38.5 | 37.3 |
| ΔE % difference between water A and B | | | 12% | | 0.7% | | 0.3% |

EXAMPLE 5

The formulation with polyphosphate also has shown the additional advantage that it can even out the distribution of color and give more uniform color as between the damaged (bleached) and virgin hair. Thus this composition can even the color distribution as between non damaged hair near the root and damaged hair near tip of the hair shaft. This is illustrated at Table 5 below with the formula 1b and 1c of example 2 (table 2) on piedment hair.

| Color | Water | | | |
|---|---|---|---|---|
| | 1 b: 0.6% EDTA | | 1 c: 0.58% STPP | |
| Parameter | Virgin Hair | Bleached Hair | Virgin Hair | Bleached Hair |
| L | 55.65 | 49.77 | 51.77 | 50.14 |
| a | 18.08 | 23.08 | 24.12 | 25.55 |
| b | 29.17 | 31.09 | 32.03 | 32.34 |
| ΔE between virgin and bleached | | 7.95 | | 2.19 |

A composition of the invention may be used as follows. The user may wet his or her hair by shampooing and rinsing, for example. Then the composition of the invention may be applied to the hair and worked through the hair as with the fingers. The composition may then be allowed to remain on the hair for about 5 to about 30 minutes to impart color to the hair. Then the composition may be rinsed from the hair and the hair may be dried. A composition of the invention may be used to color hair in other ways that are conventional to the hair coloring art such as applying to dry hair without prior shampooing.

The invention has been described with respect to several specific embodiments, but is not to be limited to those embodiments, the scope of the invention being defined by the appended claims. Various improvements, alternatives and equivalents will be apparent to those skilled in the art, and are included within the claimed invention.

What is claimed is:

1. A method for coloring hair to a red shade which comprises contacting said hair with an aqueous hair dye composition comprising:
   (A) from about 0.10% to about 10% by weight of the composition of a non-nitrogenous chelating agent selected from the group consisting of polyphosphates, phosphonates, hydroxycarboxylates, polyacrylates, zeolites and mixtures thereof;.
   (B) from about 0.01% to about 50% by weight of the composition of an oxidative dye primary intermediate comprising p-aminophenol;
   (C) from about 0.01% to about 50% by weight of an oxidative dye coupler comprising 4-amino-o-cresol; and
   (D) water.

2. A method in accordance with claim 1, wherein the non-nitrogenous chelating agent is a chelating agent that lacks an aminocarboxylic acid group or an aminophosphonic acid group.

3. A method in accordance with claim 2, wherein the chelating agent is a polyphosphate.

4. A method in accordance with claim 2, wherein the chelating agent is a phosphonate.

5. A method in accordance with claim 2, wherein the chelating agent is a hydroxycarboxylate.

6. A method in accordance with claim 2, wherein the chelating agent is a polyacrylate.

7. A method in accordance with claim 2, wherein the chelating agent is a zeolite.

8. A method in accordance with claim 7, which further comprises from about 0.01% to about 10% of amino containing chelating agents.

9. A method according to claim 1 wherein the composition further comprises a solvent selected from the group consisting of propylene glycol, isopropylene glycol and isopropanol.

10. A method according to claim 1 wherein the composition further comprises a conditioner.

11. A method according to claim 1 wherein the composition further comprises a humectant.

12. A method in accordance with claim 1, wherein the non-nitrogenous chelating agent is sodium triphosphate.

* * * * *

UNITED STATES PATENT AND TRADEMARK OFFICE
CERTIFICATE OF CORRECTION

PATENT NO.   : 6,758,866 B2
DATED        : July 6, 2004
INVENTOR(S)  : Yang et al.

It is certified that error appears in the above-identified patent and that said Letters Patent is hereby corrected as shown below:

Column 17,
Line 43, "(A) from about 0.10%" should be changed to -- (A) from about 0.1% --.

Column 18,
Line 5, "(B) from about 0.01% to about 50%" should be changed to -- (B) from about 0.01% to about 5% --.
Line 8, "(C) from about 0.01% to about 50%" should be changed to -- (C) from about 0.01% to about 5% --.

Signed and Sealed this

Seventh Day of December, 2004

JON W. DUDAS
*Director of the United States Patent and Trademark Office*